United States Patent [19]

Baumann et al.

[11] 4,101,985

[45] Jul. 25, 1978

[54] HIP-JOINT PROSTHESIS

[76] Inventors: Friedrich Baumann, Am Kirchweg 2, 8580 Neuburg-Ried, Germany; Max Bernhard Ulrich, Amselweg 55, 7900 Ulm (Donau), Germany

[21] Appl. No.: 778,931

[22] Filed: Mar. 18, 1977

[30] Foreign Application Priority Data

Mar. 20, 1976 [DE] Fed. Rep. of Germany ....... 2611985

[51] Int. Cl.² ............................................. A61F 1/24
[52] U.S. Cl. ................... 3/1.912; 128/92 C; 128/92 CA
[58] Field of Search ................... 3/1.9–1.913; 128/92 C, 92 CA

[56] References Cited

U.S. PATENT DOCUMENTS

| | | | |
|---|---|---|---|
| 2,934,065 | 4/1960 | Townley | 128/92 CA |
| 3,064,645 | 11/1962 | Ficat et al. | 128/92 CA |
| 3,228,393 | 1/1966 | Michele | 3/1.913 X |
| 3,584,318 | 6/1971 | Scales et al. | 3/1.912 X |
| 3,781,917 | 1/1974 | Mathys | 3/1.913 |
| 3,918,102 | 11/1975 | Eichler | 3/1.912 |
| 3,938,198 | 2/1976 | Kahn et al. | 3/1.912 |

FOREIGN PATENT DOCUMENTS

| | | | |
|---|---|---|---|
| 1,122,634 | 5/1956 | France | 128/92 CA |
| 2,184,159 | 12/1973 | France | 3/1.912 |
| 2,331,728 | 1/1975 | Fed. Rep. of Germany | 3/1.913 |

*Primary Examiner*—Ronald L. Frinks
*Attorney, Agent, or Firm*—Karl F. Ross

[57] ABSTRACT

A hip-joint prosthesis has a ball head shaped to fit in an acetabulum, an elongated shaft adapted to fit in and between two opposite sides of a medullary cavity of a femur, and a stem between and connecting the head to one end of the shaft. This shaft is curved in a plane and has a concave longitudinal edge and a convex longitudinal edge. A laterally projecting shoulder between the stem and the shank is engageable against a sawed-off end of a femur in whose medullary cavity the shaft is engaged. The shaft is formed on its concave edge at its two ends with inner and outer engagement surfaces of planar shape. Between these engagement surfaces on the convex side there is formed an intermediate engagement surface. When mounted in a femur the inner and outer engagement surfaces engage against one side of the medullary cavity and the intermediate engagement surface against the other for firm mounting of the shaft in the femur. Connecting surfaces incline relative to these engagement surfaces form the rest of the longitudinal edges of the shank and normally remain out of contact with the bone on which the prosthesis is mounted.

14 Claims, 10 Drawing Figures

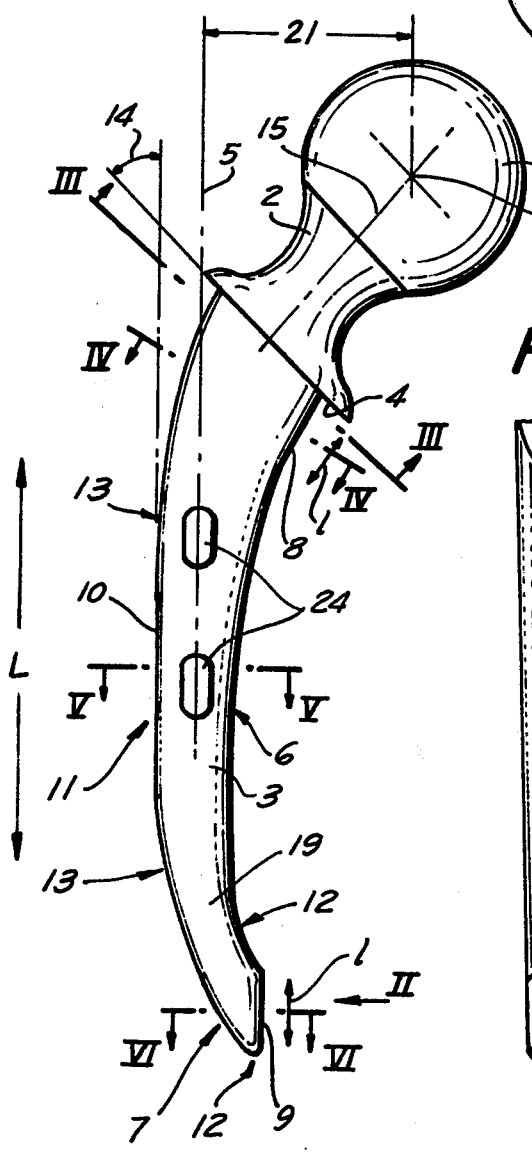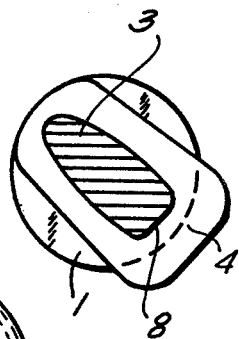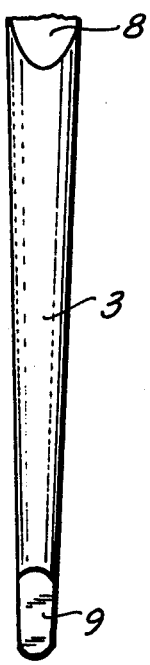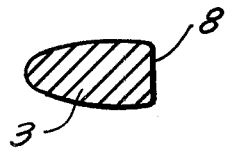

HIP-JOINT PROSTHESIS

FIELD OF THE INVENTION

The present invention relates to a prosthesis. More particularly this invention concerns a prosthesis for replacing the head and oblique neck of a femur.

BACKGROUND OF THE INVENTION

It has become standard surgical procedure to saw off the neck and head of a femur and replace them with a metal prosthesis that then acts as the upper swivel end of the femur in the acetabulum. This procedure can correct an arthritic problem, or simply replace badly broken parts of the femur.

The typical prosthesis for this surgical procedure comprises three parts: a ball head shaped to be received in the acetabulum, a stem extending from the head and forming a shoulder that bears against the sawed-off end of the femur, and a shank or shaft which extends down into the medullary cavity of the femur. The shaft or shank is typically slightly bent in a plane and the stem is bent away from the overall longitudinal axis of this shaft in order that the prosthesis accurately replace and conform to the shape of the sawed-off upper processes of the femur.

The shaft of the above-described prosthesis is set in the bored-out medullary cavity of the femur with the aid of bone cement. Thus standard procedure has always been to use a shaft which is spaced all around from the inside wall of the femur, filling the lateral interstices between the shaft of the prosthesis and the inside wall of the femur in the medullary cavity thereof with bone cement.

Such mounting has proven troublesome in many situations. In particular, due to the enormous stresses which this particular prosthesis is subjected to, so-called micromovements of the prosthesis relative to the femur often soon translate themselves into dangerous looseness. Thereupon it is necessary to operate again on the patient and reset the loose prosthesis.

OBJECTS OF THE INVENTION

It is therefore an object of the present invention to provide an improved prosthesis of the above-described general type.

It is another object of the invention to provide such a prosthesis which can be rigidly set in the femur and which is unlikely to loosen therein, even when subjected to the greatest possible strains.

SUMMARY OF THE INVENTION

These objects are attained in accordance with the present invention in a prosthesis of the above-described general type wherein the concave longitudinal edge of the shaft of the prosthesis is formed adjacent the femur-engaging shoulder and at its free tip with inner and outer engagement surfaces which are engageable with the bone of one side of the medullary cavity of the femur. Between these engagement surfaces and on the convex longitudinal edge of the shaft there is formed an intermediate engagement surface which is engageable with the bone of the other side of the medullary cavity of the femur and which is generally parallel to the outer engagement surface on the concave side. Connecting surfaces to each longitudinal side of and inclined to each of the engagement surfaces form the rest of the longitudinal edges of the shaft and normally lie out of contact with the bone of the femur in which the shaft is engaged and against which the engagement surfaces bear directly.

Thus in accordance with the present invention the shaft of this prosthesis is dimensioned so that its opposite longitudinal edges bear against opposite longitudinal sides in the medullary cavity. In this manner a three-surface engagement between the prosthesis and the femur is obtained so that an extremely rigid and sound anchoring of the prosthesis in the femur is ensured. It is therefore possible to mount this prosthesis without the use of bone cement, thereby eliminating a potential cause for allergic reaction, without in any way obtaining a less secure mounting of the prosthesis in the bone. The space left in the medullary cavity between the shaft of the prosthesis and the bone can be filled with bony integumentary material which will quickly grow and itself fill the space, tightly anchoring the totally inert metal shaft of the prosthesis in the living portion of the bone.

According to further features of this invention, the cross-sectional area of the shaft increases toward the ball, allowing the space between the shaft and the bone easily to be filled as described above. Furthermore each of the engagement surfaces is flat, lying in a plane, and the connecting surfaces between them are arcuate and rounded. The intermediate surface on the convex edge of the shaft of the prosthesis is approximately twice as long in the longitudinal direction of the shaft as the outer or inner engagement surface, so that overall approximately the same amount of bearing surface is provided upon one edge of the shaft of the prosthesis as on the other.

In order to reduce the lever effect operating on the prosthesis as much as possible and also to reduce the overall size of the prosthesis, the head is of the largest possible diameter and the neck or stem connecting it to the shank is of minimum length so that the spacing between the center of the ball head and the longitudinal middle axis of the shaft is at most 25 mm. The shaft is also formed with laterally throughgoing holes so that bone material as described above can grow directly through the shaft and anchor the prosthesis rigidly inside the femur.

According to further features of the invention a rigid securing of the prosthesis in the femur is ensured further by forming an internally threaded blind bore in the prosthesis which extends longitudinally along the neck and terminates generally inside the ball head, so that it opens on the shaft or shank of the prosthesis in a downward direction when the arrangement is mounted. A corresponding hole is drilled below the major trochanter in line with this bore so that a bolt can be threaded through the two holes, preferably with interposition of a specially formed washer head under the bolt, thereby prestressing the entire prosthesis against the trochanter major and eliminating even the possibility of tiny motions of the prosthesis relative to the bone.

It is also possible, in accordance with this invention, to employ an artificial acetabulum exactly dimensioned to fit over the head of the prosthesis. To this end, the original acetabulum may be slightly enlarged, or a reduced ball head can be used so that the new acetabulum, having a wall thickness of approximately 4 mm, can be merely set in the old acetabulum and screwed in place. For this purpose it is possible to form a counterbore around the edge of the acetabulum in which is received a rim or tabs projecting radially from the artificial acetabulum so that the new structure can be snugly secured inside the ischium, ilium and pubis and form a perfectly dimensioned new acetabulum. Such a procedure is particularly useful when the prosthesis according to this invention is employed to correct an arthritic condition wherein bony matter has built up in the acetabulum so as to make it nonround.

BRIEF DESCRIPTION OF THE DRAWING

FIG. 1 is a side view of a prosthesis according to this invention;

FIG. 2 is a detail view taken in the direction II — II of FIG. 1;

FIGS. 3, 4, 5 and 6 are sectional views taken along lines III — III, IV — IV, V — V and VI — VI, respectively, of FIG. 1;

SPECIFIC DESCRIPTION

Figure 7:
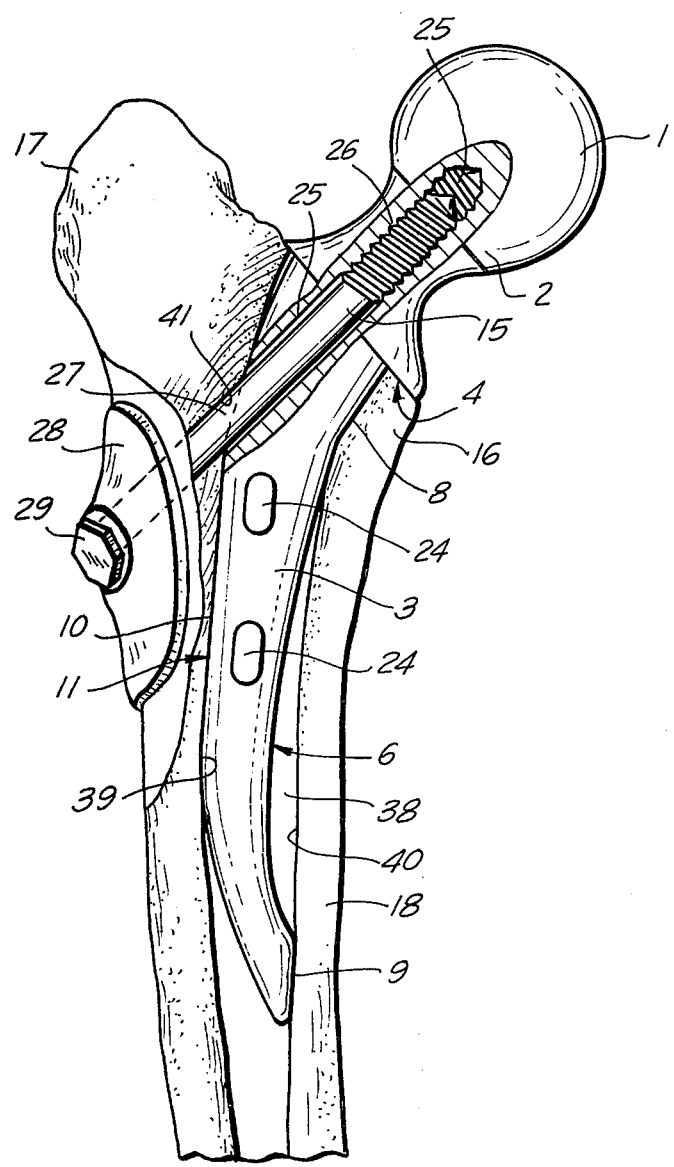
FIG. 7 is a side view partly in section showing mounting of the prosthesis according to this invention.

As shown in FIGS. 1-6 the prosthesis according to the present invention basically comprises a part-spherical ball head 1, a doubly outwardly flared neck or stem 2 extending from the head 1, a shank 3 extending downwardly away from the other end of the stem 2, and a shoulder formation 4 between the stem 2 and the shank 3.

The shaft 3, although curved, has a longitudinal axis 5 and the stem 2 also is centered on an axis 15 which extends at an angle of slightly more than 90° from the axis 5. This axis 15 of the stem 2 passes through the center of curvature 20 of the head 1. Thus the shaft 3 is curved in a plane including the axis 5 and in FIG. 1 constituting the plane of the view.

The shaft 3 according to this invention has an inner concave longitudinal edge 6 extending from the shoulder 4 and terminating at a tip 7. This edge 6 is formed adjacent the shoulder 4 with a flat inner engaging surface 8 and at the tip 7 with another flat engagement surface 9 that itself lies in a plane parallel to the axis 5. On the convex outer longitudinal edge 11 of the shank 3 there is a flat intermediate engagement surface 10 lying in a respective plane again parallel to the axis 5 and here having an overall length L of approximately twice the length l of the surfaces 8 and 9, which are both approximately the same overall length. Between the flat surfaces 8 and 9 on the inner edge 6, this edge 6 is constituted pletely by a curved and nonflat surface 12 which is inclined to the surfaces 8 and 9 and in no region planar. Simulary to either longitudinal side of the flat engagement surface 10 the edge 11 is formed with curved and nonplanar connecting surfaces 13 that once again are inclined to this surface 10.

As mentioned above, the engagement surfaces 9 and 10 are parallel to each other and to the longitudinal axis 5 of the shaft 3. The shoulder 4 is inclined at an angle 14 of approximately 45° to the axis 5 and the longitudinal axis 15 of the stem 2 is nearly perpendicular to the shoulder 4. The surface 8 adjacent the shoulder 4 is inclined relative to the axis 5 so as to fit snugly as shown in FIG. 7 against the trochanter minor 16 of a femur 18 whose trochanter major is shown at 17. FIG. 7 shows clearly how the planar surfaces 8, 9 and 10, which all lie in planes perpendicular to the plane of curvature of the shaft 3, lie snugly against the corresponding sides of the medullary cavity 38 of the femur 18. More particularly, the surface 10 lies snugly against one inner side 39 of the medullary cavity and the surfaces 8 and 9 both lie snugly against the other opposite side 40 of this cavity 38. The end region 19 adjacent to the tip 7 is bent much more severely than the rest of the shaft 3 so as to establish this exact positioning.

When setting the prosthesis in the femur 18 as shown in FIG. 7 there is no need to employ any bone cement. Indeed, merely before insertion of the shaft 3 in the prepared femur a mass of the patient's own bone material in ground-up condition is inserted in the bored-out medullary cavity 38 so that the shaft 3 will indeed become set in living matter after a short period of time. The prosthesis is positioned so that the center 20 of the head 1 lies at a spacing 21 from the longitudinal center line in axis 5 of shank 3 which in use lies on the center line 22 of the femur 18. This spacing 21 is normally no greater than 25 mm, although it is possible for a very large patient to have a prosthesis so dimensioned that the distance 21 is as much as 42 mm.

Figure 10:
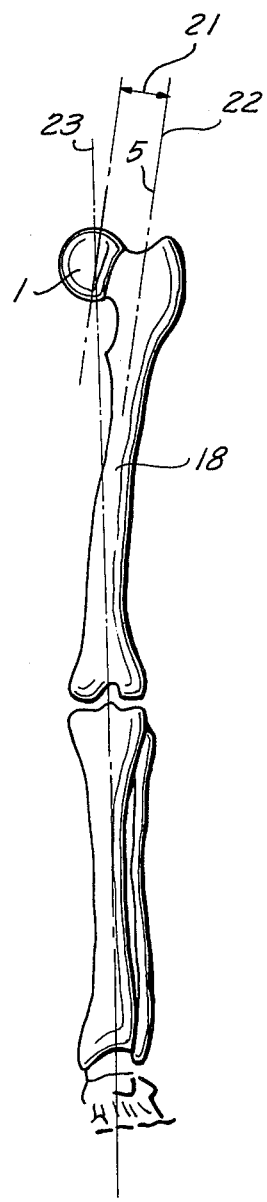
FIG. 10 is a small-scale view showing the prosthesis according to this invention relative to the bones of a leg in which it is mounted.

FIG. 10 shows a vertical line extending through the center 20 and the center of the foot bones of a leg having a femur 18. It is clear that the offset 21, which is relatively slight, can readily be the above-given relatively small dimension without danger of breaking of the prosthesis.

The shank 3 is formed with lateral throughgoing holes 24 through which living bone material can grow as described above. In addition the prosthesis is formed with a bore 25 extending along the axis 15 and threaded at its end 26 inside the stem 2 and head 1. A steel screw 27 extends into this bore 25 and through a bore 41 formed in line with the bore 25 below the trochanter major 17 of the femur 18. The outer end of this bore 27 has a head 29 that bears by means of a specially formed washer plate 28 on the outside of the bone 18. Such mounting allows a prosthesis to be prestressed against the bone 18 and ensures that even so-called micromovements of the prosthesis relative to the bone 18 are impossible.

Figure 8:
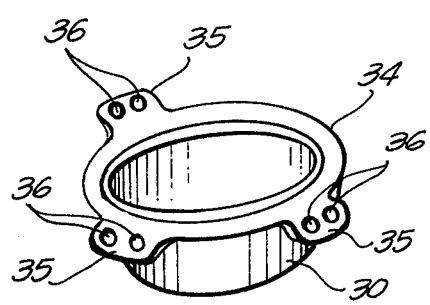
FIG. 8 is a perspective view showing another part of the prosthesis according to this invention.
Figure 9:
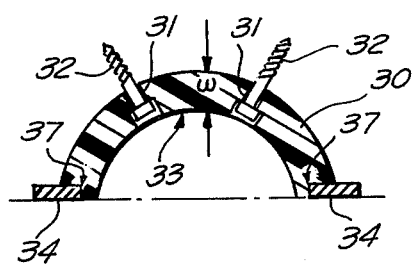
FIG. 9 is a section through the part shown in FIG. 8.

FIGS. 8 and 9 show an artificial acetabulum formed of heat-resistant synthetic-resin material, here polytetrafluoroethylene, and having a wall thickness w of between 3 mm and 5 mm, here 4 mm. The unit is formed as a part-spherical cup 30 having radially throughgoing counterbored holes 31 adapted to receive screws 32 that are set in the bones forming the acetabulum of the patient. Only two such holes 31 are necessary. In addition the unit is provided with an external holding ring 34, itself formed as best shown in FIG. 8 with a plurality of radially extending tabs 35 each having two throughgoing holes 36 again adapted to receive screws. These tabs 35 are not angularly equispaced about the rim of the cup 30, but are so positioned as to lie against the thickest parts of the bones — the ischium, ilium and pubis — forming the acetabulum. Furthermore, the ring 34 is set in a radially outwardly open groove 37 of the cup 30 so that it lies coplanar with the face of the cup 30. This ring 34 is metallic.

Thus with the prosthesis according to the present invention it is possible to replace the upper bony processes on the femur 18 and to reline the acetabulum. In this manner a completely new hip joint can be provided for a patient in order to correct an arthritic condition or to replace a badly broken bone. The new parts will be firmly and permanently anchored in the patient. The nonuse of bone cement will eliminate potential hazard of allergic reaction, yet in no way weaken the mounting of the parts in the bones of the patient.

We claim:

1. A prosthesis comprising a ball head shaped to fit in an acetabulum, an elongated shaft shaped to fit in and between the two opposite sides of a medullary cavity of a femur, and a stem between and connecting said head to one end of said shaft, said shaft being curved in a plane and having a concave longitudinal edge and a convex longitudinal edge and said stem being inclined in said plane to the longitudinal axis of said shaft, said prosthesis being formed with:
 a laterally projecting shoulder engageable against a sawed-off end of a femur in whose medullary cavity said shaft is to be engaged;
 an inner engagement surface on said concave edge adjacent said shoulder and engageable with one of said sides of a medullary cavity of said femur;
 an outer engagement surface on said concave edge at the other end of said shaft and engageable with said one side of a medullary cavity of said femur;
 an intermediate engagement surface on said convex edge between said inner and outer engagement surfaces and generally parallel to said outer engagement surface, said intermediate engagement surface being engageable with the other side of a medullary cavity of said femur; and
 a connecting surface to each longitudinal side of and inclined to each of said engagement surfaces and normally adapted to lie out of contact with the sides of said medullary cavity.

2. The prosthesis defined in claim 1 wherein said inner engagement surface is inclined to said longitudinal axis.

3. The prosthesis defined in claim 2 wherein said engagement surfaces of each generally planar and generally perpendicular to said plane.

4. The prosthesis defined in claim 2 wherein said intermediate engagement surfaces is at least twice as long measured parallel to said axis as said outer engagement surface.

5. The prosthesis defined in claim 4 wherein said inner engagement surface is of generally the same length measured in said plane as said outer engagement surface.

6. The prosthesis defined in claim 5 wherein said connecting surfaces immediately adjacent said outer engagement surface on said concave edge forms a larger angle with said outer engagement surface than any of the other connecting surfaces form with their respective engagement surfaces.

7. The prosthesis defined in claim 1 wherein the center of said ball head is spaced at most 25mm from said axis.

8. The prosthesis defined in claim 1 wherein said shaft is formed with throughgoing bores transverse to said plane.

9. The prosthesis defined in claim 1 wherein said prosthesis is further formed with a threaded blind bore opening in a direction in line with said stem away from said head, said prosthesis further comprising a threaded screw engageable in said bore.

10. The prosthesis defined in claim 1, further comprising a cup-shaped acetabulum lining shaped to fit over said ball head and constituted of heat-resistant synthetic-resin material with at least one throughgoing bore adapted to receive a screw for anchoring said lining in an acetabulum.

11. The prosthesis defined in claim 10 wherein said lining was a wall thickness of between 3 mm and 5 mm.

12. The prosthesis defined in claim 11 wherein said wall thickness is substantially 4 mm.

13. The prosthesis defined in claim 10 wherein said cup-shaped lining has a radially extending flange formed with throughgoing mounting holes adapted to receive screws.

14. The prosthesis defined in claim 13 wherein said lining is formed with a peripheral groove and has a holding ring constituting said flange recessed in said groove.

* * * * *